United States Patent [19]

Pretlow, III

[11] 3,984,093
[45] Oct. 5, 1976

[54] ANATOMICAL LUMBAR POSITIONER FOR VERTEBRATE BEINGS

[76] Inventor: Robert A. Pretlow, III, 300 Foxridge Road, Lexington Park, Md. 20653

[22] Filed: Aug. 26, 1975

[21] Appl. No.: 607,760

[52] U.S. Cl. .............................................. 269/328
[51] Int. Cl.² ......................................... A61G 13/00
[58] Field of Search ............. 269/322, 328; 128/134

[56] References Cited
UNITED STATES PATENTS

| | | | |
|---|---|---|---|
| 1,622,313 | 3/1927 | Gellhorn | 269/328 |
| 2,577,177 | 12/1951 | Anderson | 269/322 |
| 2,668,577 | 2/1954 | Vanderschel | 128/134 |
| 2,764,150 | 9/1956 | Ettinger et al. | 269/328 |
| 3,829,079 | 8/1974 | Fox | 269/328 |
| 3,892,399 | 7/1975 | Cabansag | 269/328 |

*Primary Examiner*—Al Lawrence Smith
*Assistant Examiner*—Robert C. Watson
*Attorney, Agent, or Firm*—J. Gibson Semmes

[57] ABSTRACT

In the medical treatment and examination of animate patients, means to flex and secure a spinal column against movement, exclusive of applying pressure to the head and/or neck, comprising coactively adjustable seat and shoulder engaging elements, arranged to flex the spinal column in an optimum posture of flexure, while simultaneously restraining the patient against movement of his spinal column. Coactive plates engaging patient's shoulders and the seat under and around the pelvis are compressed while the patient is strapped therein, whereby the vertebral column is bowed posteriorly, thus widening the intervertebral space for introduction of the spinal tap needle therein. The mechanism permits the patient's pelvis to be advanced anteriorly so that it is sustained in the same vertical plane as the shoulders, whereby flexion of the vertebral column is obtained, instead of leaning the patient out of vertical axis, a normal vertical or horizontal axis.

2 Claims, 3 Drawing Figures

ANATOMICAL LUMBAR POSITIONER FOR VERTEBRATE BEINGS

BACKGROUND OF THE INVENTION

Whereas the invention is defined with reference to applicability to the anatomy of an infant patient, it will be clear to those skilled in the field that it may be applicable to any animate vertebrate having need of flexure immobilization, more especially to perform the technique of the spinal tap whereby one inserts a needle in the space between two of the vertebrae in the lower or lumbar region of the back and into the spinal fluid sac. The dangers inherent in failure to satisfactorily perform the spinal tap, because of movement of the patient or inadequate flexure of the spine are well known. Clearly, it is important to tap the spinal fluid which surrounds the spinal cord without damage to the nerves of the latter, which are nourished by the fluid within the spinal fluid sac. The invention is therefore most suitably adapted to the young child or infant, who is incapable of cooperation and who heretofore has been generally held in the proper flexed position by an adult assistant.

In the art, two methods are employed as infants in the upright position are engaged by an assistant with thumbs at the shoulders, simultaneously holding onto the upper legs with the fingers. This requires extraordinary strength, and size of hands, a characteristic possessed by few nurses. Otherwise, the infant is laid on its side and with one arm behind his neck, embraced posteriorly to flex the spine. The disadvantages through this latter method may be listed as follows. It is difficult to observe cessation of breathing, vomiting or other discomfiture, and there is extraordinary pressure imposed upon the child's neck, resulting occassionally in injury. In the sidewise position it is also difficult to orient the needle perpendicularly with respect to the skin, etc. Accordingly, a mechanical device for permitting flexure of the spine while the child is sitting up is desirable, as is such a device as would preclude pressure on the neck, during the course of flexure of the spine.

DESCRIPTION OF THE PRIOR ART

The infant holders of Lune U.S. Pat. No. 3,034,502 dated May 15, 1963 and 3,606,885, dated Sept. 21, 1971 are restricted to general immobilization for operative purposes and have no relation to the primary objective of the invention herein. Similar are the restraining devices of Arp U.S. Pat. No. 3,306,287 dated Feb. 28, 1967 and Kolar 3,223,084 dated Dec. 14, 1965, the former being adapted to support the patient on an operating table, which itself may be movable relative to the horizontal or vertical. Perhaps the most advanced concept in the present field is represented by Fox in Patent 3,829,079 dated Aug. 13, 1974. In none of the art, either singly or combined, can the objectives of the present invention be reached for a normally uncooperative, uncontrollable vertebrate such as an infant. Additionally, in the known systems such as have been hereinbefore described and in the techniques currently practiced by attendants with and without equipment, the danger of injury to the spinal column through the excessive application of pressures as to such portions of the anatomy as the neck are indeed replete with risks. It is to obviate these risks and to perform the improved function of presenting an infant adequately for a safe and immobile flexed position that the invention is directed.

DESCRIPTION OF THE PREFERRED EMBODIMENTS

Figure 1:
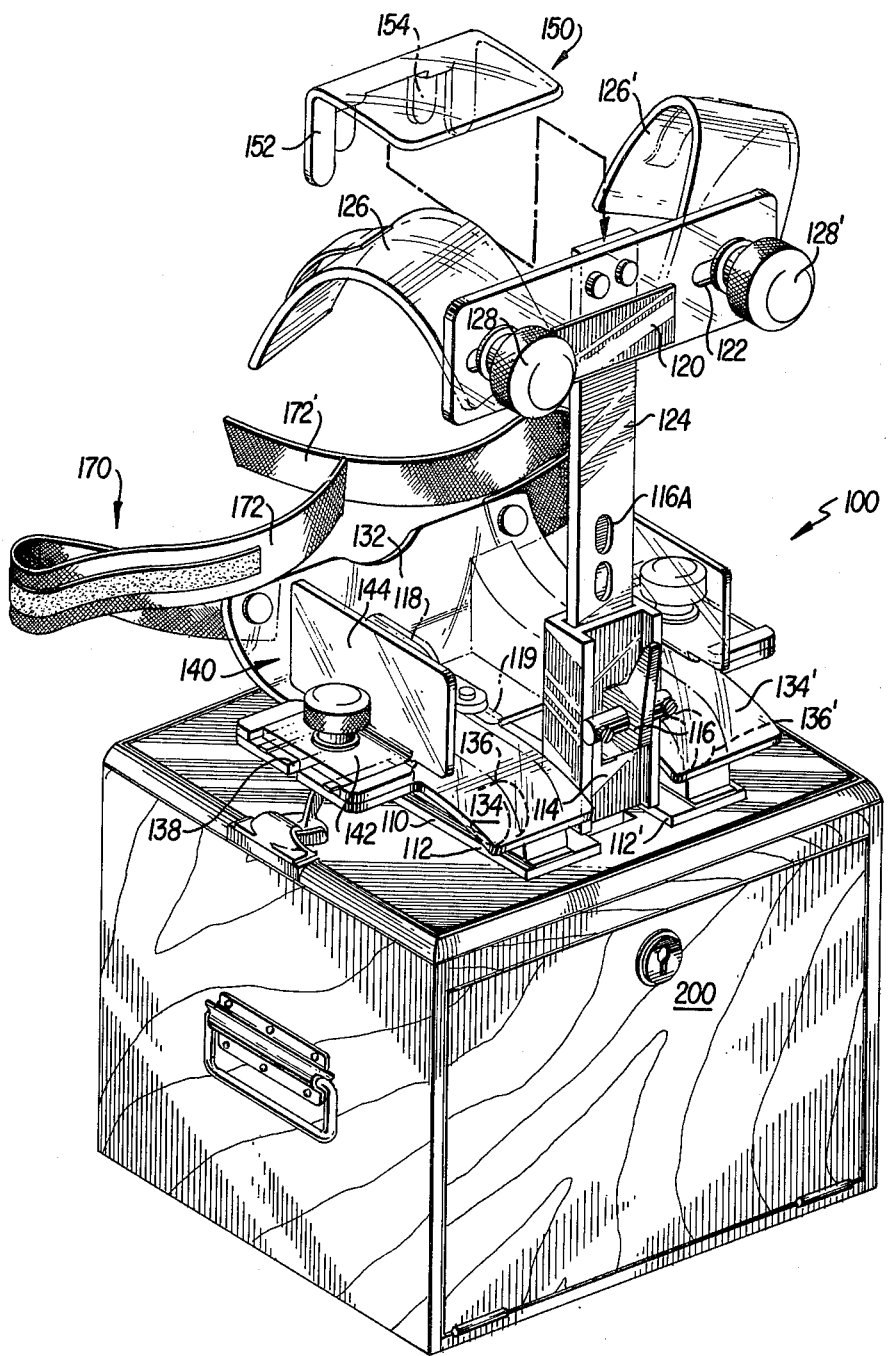
FIG. 1 is a view in perspective of the invention.
Figure 2:
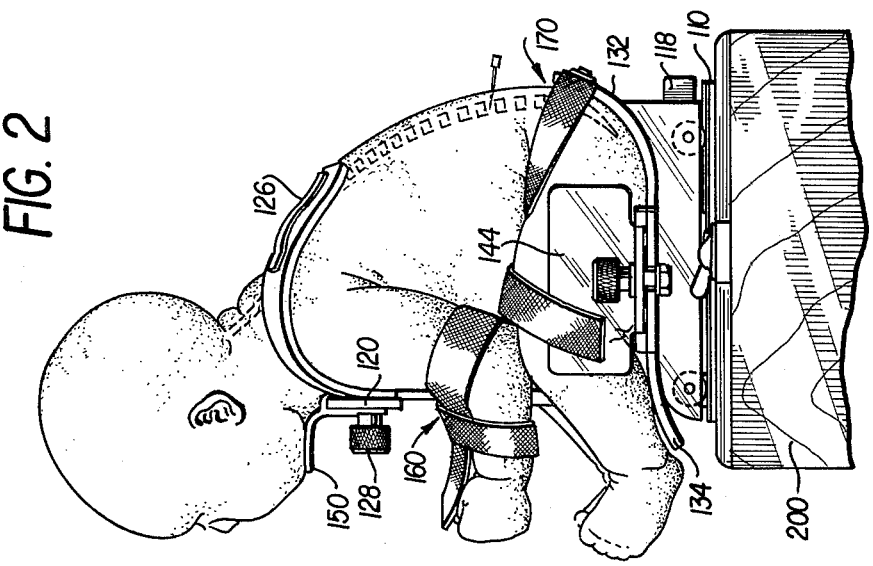
FIG. 2 is a view in side elevation of the invention as adapted to an infant.

With reference, particularly to FIGS. 1 and 2, the lumbar puncture seat 100 is mounted upon a base 110 which said base is adapted to support in adjustable relation thereto the vertical compression component 120 and the horizontally adjustable support component 130, said components being respectively adapted to the shoulders and to the seat of the patient. His vertebral column may be flexed as shown in FIG. 2 to ensure a bowing of the column posteriorly, thus widening the inter-vertebral space and facilitating accurate penetration of the spinal needle during the spinal tap technique.

The detailed construction of the basic components may be defined substantially as follows: base 110 fixes parallel seat slide tracks 112 and 112', said tracks being disposed on either side of a substantially forwardly placed, centrally located ratchet column 114, said column having a suitable compression release lever 116 for engaging corresponding ratchet depressions 116A in the compression guide bar 124 of the shoulder engaging assembly 120. Rearwardly of the ratchet column and also fixed to the base 110 is a seat adaptable release lever 118. The seat is adapted to forward and aft movement relative to the ratchet column and it is seat slide stop lever 118 which will fix the seat in the desired position, relative to the vertical compression component as will be hereinafter described. The seat slide stop lever 118 may comprise any suitable means for frictional arresting and positioning of the seat.

The anatomical support member or seat 130 thus defines an upward curvilinear rear end 132 having an arcuate cut-out which is substantially central thereof, said curvilinear end extending beyond the horizontal as shown in FIG. 1. The horizontal portion terminates forwardly and downwardly to form curved extensions 134 and 134', said extensions being spaced apart to clear ratchet column 114, and forming thereabout a gap which is sufficient to permit substantial sliding movement of the seat, relative to the column. Mounted also within the seat may be plural rollers 136, permitting a friction-free fore and aft, sliding relationship between the seat and the base.

Again, seat 130 is provided with lateral extensions, defining transverse slots 138 and 138' (not shown), permitting slidably adjustable relation between corresponding lateral thigh plates and the seat, per se, as will be hereinafter described. By reference to FIG. 2 it will be apparent that the lateral thigh plates 140 and 140' are respectively adapted to contact the exterior thighs of the infant, to restrain such movement as might disturb the desired, fixed flexure posture of the spine as shown in phantom. These plates 140 and 140' each comprise horizontal and vertical extensions 142 and 144', the extension 142 having rails beneath and seating the compression lock for each lateral thigh plate.

Thus, in cooperation with the seat track extension slot 138 movement may be obtained and lateral adjustment made to the plates 140 prior to locking in position.

Referring to the means for securing the shoulders of the patient, relative to the fixed base 110, the vertical compression component 120 is shown to define sidewise apertures 122 and 122', each of said apertures being adapted to facilitate coactive positioning of the shoulder-engaging clamps 126 and 126'. The arrangement between the shoulder clamps 126 and 126' and their supporting anchor 120 is such that the shoulder plates themselves may be moved transversely, relative to the center post 124, and/or arcuately to conform to the individual conformation of the patient involved. Additionally, the shoulder plate anchor 120 is adapted to secure the chin plate 150 when required for upright retention of the patient's head.

Figure 3:
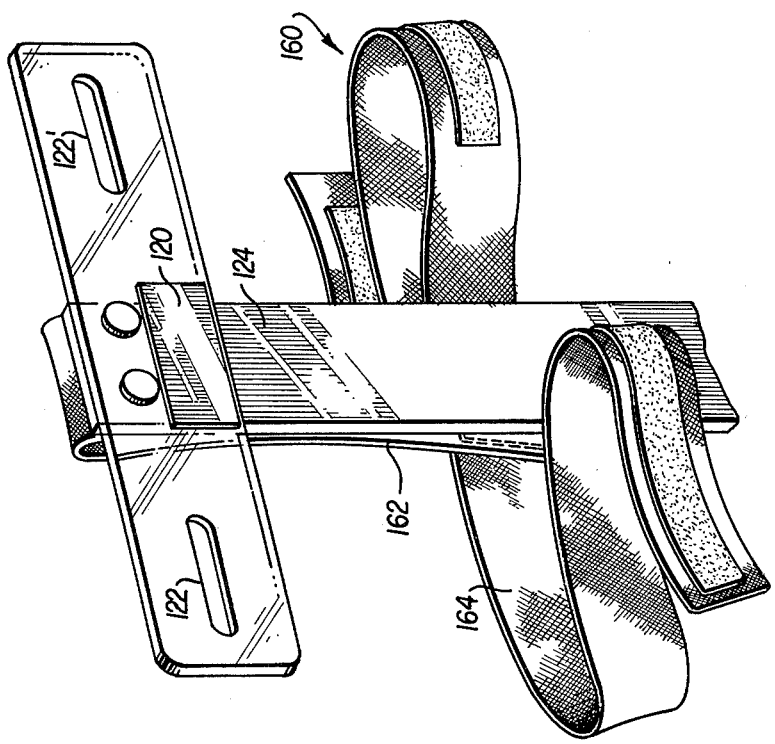
FIG. 3 shows an enlarged perspective of a portion of the shoulder engaging compression guide bar and associated shoulder plate and arm restraining straps.

One further accoutrement to the vertical compression complex comprises the restraining strap 160 having extensions 162 and 164, emanating from a vertically disposed pendant 162. Reference FIG. 3.

In practice and with especial reference to FIG. 2, it will be seen that a patient has the lower portion of his body, initially restrained by use of the hip-engaging restraining belt 170 comprising the extensions 172, 172' and the thigh contacting lateral thigh plate series 140–140'. The seat has theretofore been set in longitudinal position by tightening the clutch bolt of the seat slide 118, against the lower top surface of the seat adjacent slot 119 thereof.

Upon essential adjustment of the respective vertical compression component 120 and horizontal seat component 130, the correct posture or spine flexure is obtained. Once obtained, the respective compression guide bar is held by means of the compression release ratchet lever mechanism 116 and the torso is thus secured immobile. In effect, the applied flexure caused by the compression force causes a vertebral ligament counter-action or spring force, and it is the balance, so to speak between these opposed forces that precludes movement of either spine or shoulders, even without straps. The seat has theretofore been set in longitudinal position by the locking adjustment of the seat slide stop lever 118, relative to the slot 119 of the seat. The strap 160 serves to restrain movement of the patient's arms, thereby avoiding disturbance with the function of puncture or contamination of the field.

Whereas the device is shown with a support-container 200, it may be used equally as well without the support and the infant placed on its side for the spinal tap function to be performed. Since the patient is essentially totally contained by the device it may also be used upside down, such as in special X-ray procedures in which spinal taps are made with injection of radiologically-opaque material into the spinal fluid. The opaque material (which is heavy) will then sink to the lowest point of the spinal space and if the child is turned upside down it will flow towards the head, outlining on an X-ray the upper spinal space as well as the lower and central part of the brain. The device therefore has utility in the broader fields of radiology and/or general pediatrics and may extend, as well to broader fields of medicine wherein anaesthesia or injury causes a lack of cooperative ability from the patient.

I claim:

1. A medical aid to the immobile positioning of anatomy of animate vertebrate beings, comprising in combination a portable base member:
   A. vertically extensible compression member, mounted on the base member, said compression member including variable positioning locking means connecting base and compression member and means on the compression member restrainedly engageable with the shoulders of the being;
   B. anatomical support member, superposed upon the base for horizontal translation relative thereto and in extenso-contractu positioning, relative to the compression member, and variable position locking means connecting the base and support member, whereby upon vertical and horizontal adjustment of the respective compression and support members relative to each other, the vertebral column of the being may be compressed between its shoulder and buttocks, to bow its vertebral column posterially into a posture of desired flexure, without applying pressure to the spine, above the area which is immediately adjacent the shoulders;
   C. plural thigh contacting plates mounted upon the anatomical support, said plates having transverse adjustability, relative to the anatomical support member.

2. A medical aid to the immobile positioning of anatomy of animate vertebrate beings, comprising in combination:
   A. a portable base member;
   B. vertically extensible compression member mounted on the base member, said compression member including means restrainedly engageable with the shoulders of the being and variable position locking means;
   C. anatomical support member, superposed upon the base for horizontal translation relative thereto and in extenso-contractu positioning, relative to the compression member, said support member including variable position locking means, said anatomical support further bearing thigh contacting plates, said plates having transverse adjustability relative to the anatomical support member; and
   D. chin support means, mounted upon the compression member adjacent the means restrainedly engageable with the shoulders of the being, whereby upon vertical and horizontal adjustment of the respective compression, support members an associated chin support and thigh contacting plates, and upon vertical and horizontal adjustment of the respective compression and support members relative to each other, the vertebral column of the being may be compressed between its shoulder and the buttocks, to bow its vertebral column posteriorly into a posture of desired flexure, without applying pressure to the spine, above the area which is immediately adjacent the shoulders.

* * * * *